(12) United States Patent
Brach (10) Patent No.: US 8,076,943 B2
(45) Date of Patent: Dec. 13, 2011

(54) IMPEDANCE-BASED ARC DETECTOR FOR COMPUTED TOMOGRAPHY SCANNER AND METHOD OF USE THEREOF

(75) Inventor: William E. Brach, Cary, IL (US)

(73) Assignee: Genesis Medical Imaging, Inc., Huntley, IL (US)

(*) Notice: Subject to any disclaimer, the term of this patent is extended or adjusted under 35 U.S.C. 154(b) by 372 days.

(21) Appl. No.: 12/390,016

(22) Filed: Feb. 20, 2009

(65) Prior Publication Data

US 2009/0212786 A1    Aug. 27, 2009

Related U.S. Application Data

(60) Provisional application No. 61/030,317, filed on Feb. 21, 2008.

(51) Int. Cl.
  *G01R 31/08* (2006.01)
(52) U.S. Cl. .............. 324/525; 324/536; 378/4
(58) Field of Classification Search .......... 324/36, 324/42, 44, 509, 525, 536, 544, 762; 378/4, 378/17, 98, 101, 117, 118, 207, 410; 702/58–62, 702/121–123; 188/136, 166
See application file for complete search history.

(56) References Cited

U.S. PATENT DOCUMENTS

| | | | |
|---|---|---|---|
| 4,356,443 A | 10/1982 | Emery | |
| 4,520,495 A * | 5/1985 | Tanaka | 378/117 |
| 5,105,456 A | 4/1992 | Rand et al. | |
| 5,305,363 A | 4/1994 | Burke et al. | |
| 5,347,571 A * | 9/1994 | Furbee et al. | 378/105 |
| 5,432,455 A | 7/1995 | Blades | |
| 5,978,446 A | 11/1999 | Resnick | |
| 6,362,629 B1 | 3/2002 | Parker et al. | |
| 6,504,892 B1 | 1/2003 | Ning | |
| 6,522,721 B1 | 2/2003 | Lustberg | |
| 6,747,459 B2 | 6/2004 | Parker et al. | |
| 6,772,077 B1 | 8/2004 | Parker et al. | |
| 6,882,703 B2 * | 4/2005 | Price et al. | 378/91 |
| 6,972,572 B2 | 12/2005 | Mernyk et al. | |
| 6,975,698 B2 | 12/2005 | Katcha et al. | |
| 6,987,389 B1 | 1/2006 | Macbeth et al. | |
| 7,114,850 B2 * | 10/2006 | Dong et al. | 378/207 |

(Continued)

FOREIGN PATENT DOCUMENTS

JP    2004-259504    9/2004

OTHER PUBLICATIONS

Partial Translation of JP 2004-259504, two pages,PDF file attached.*
Genesis Medical Imaging,Inc. news release on Dec. 2007 (pdf file attached ).*

*Primary Examiner* — Timothy J Dole
(74) *Attorney, Agent, or Firm* — Vedder Price, P.C.

(57) ABSTRACT

The present disclosure relates to an impedance-based arc detector for CT scanners and method of use and diagnosis therewith, and more specifically, to a two- or three-way conductive probe detector system and associated signal processing unit to distinguish the location of arc faults on a CT scanner at either the high-voltage cable of an x-ray tube, an anode connected to the x-ray tube, a cathode also connected to the x-ray tube, a high-voltage well, or a power distribution unit of the tube.

12 Claims, 11 Drawing Sheets

U.S. PATENT DOCUMENTS

| | | |
|---|---|---|
| 7,259,568 B2 | 8/2007 | Mernyk et al. |
| 7,302,041 B2 | 11/2007 | Deuringer et al. |
| 7,366,280 B2 | 4/2008 | Lounsberry |
| 7,640,120 B2 * | 12/2009 | Axenbeck et al. .............. 702/58 |
| 2002/0125892 A1 | 9/2002 | Parker et al. |
| 2004/0156153 A1 | 8/2004 | Csanky et al. |
| 2006/0038574 A1 | 2/2006 | Wayman et al. |
| 2007/0262780 A1 | 11/2007 | Mernyk et al. |

* cited by examiner

Primary Spit Event, (Date, Hour), Anode Tank
Secondary Spit Event, (Date, Hour), X-Ray Tube
Primary Spit Event, (Date, Hour), X-Ray Tube
Primary Spit Event, (Date, Hour), Anode Tank
Secondary Spit Event, (Date, Hour), X-Ray Tube
Primary Spit Event, (Date, Hour), X-Ray Tube
Primary Spit Event, (Date, Hour), Anode Tank
Secondary Spit Event, (Date, Hour), X-Ray Tube
Primary Spit Event, (Date, Hour), X-Ray Tube
Primary Spit Event, (Date, Hour), Anode Tank
Secondary Spit Event, (Date, Hour), X-Ray Tube
Primary Spit Event, (Date, Hour), X-Ray Tube
Primary Spit Event, (Date, Hour), Anode Tank
Secondary Spit Event, (Date, Hour), Cathode Tank
Primary Spit Event, (Date, Hour), Cathode Tank
Primary Spit Event, (Date, Hour), Anode Tank
Secondary Spit Event, (Date, Hour), Cathode Tank
Primary Spit Event, (Date, Hour), Cathode Tank
End of Records Total Tube Spit Count = 00008
Total Anode Tank Spit Count = 00006
Total Cathode Tank Spit Count = 00004

100
IMPEDANCE-BASED ARC DETECTOR FOR COMPUTED TOMOGRAPHY SCANNER AND METHOD OF USE THEREOF

CROSS-REFERENCE TO RELATED APPLICATION

This application claims the benefit of and priority from U.S. Provisional Patent Application No. 61/030,317, filed on Feb. 21, 2008, entitled IMPEDANCE-BASED ARC DETECTOR FOR COMPUTER TOMOGRAPHY SCANNER, which application is expressly incorporated herein by reference.

FIELD OF THE DISCLOSURE

The present disclosure relates to an impedance-based arc detector for computed tomography scanners and a method of diagnosis therewith, and more specifically, to a two- or three-way conductive probe detector system and associated signal processing unit to distinguish the location of arc faults on a CT scanner at either the high-voltage cable of an x-ray tube, an anode connected to the x-ray tube, a cathode also connected to the x-ray tube, a high-voltage well, or a power distribution unit of the tube.

BACKGROUND

CT scanners, also known as Computed Axial Tomography scanners (CAT scanners), rotate a two-dimensional x-ray source around a human body. An x-ray lamp captures a plurality of flat images of the body as it moves through space in a fixed configuration. Computer-assisted reconstruction algorithms allow for digital reconstruction and the determination of useful slice images of a patient seen longitudinally from the original images taken orthogonal to the human standing axis. Since the 1930s, many types of CT scanners have been developed, such as Inverse Geometry CT, 256+ Slice CT, Dual Source CT, Multislice CT, Helical or Spiral CT, or Electron Beam CT.

At the heart of CT scanning technology lies an x-ray source acting as a radiation source operating in the wavelength in the range of 10 to 0.01 nm. These waves are capable of partial absorption by the human body. Because different parts of the body have different densities and absorption coefficients to the radiation, CT scanners can reconstruct images where the position of these different parts can be viewed from within the human body. When x-rays are shot through the body, an image is recorded on the other side of the body indicating zones where absorption was the greatest. Most CT scanners use x-ray tubes for producing the source radiation.

X-ray tubes are made of a glass bulb where a vacuum is created between an anode and a cathode separated by a small distance. By applying sufficient voltage between the anode and the cathode, electrons jump in the vacuum. In one model of x-ray tube, a layer of tungsten or molybdenum is placed upon the surface of the anode to produce degraded x-rays perpendicular to the anode surface as a byproduct of the absorption of electrons into the anode. The transformation process only produces 1% of x-rays and 99% of heat at the anode. To be powerful enough to map the human body, the x-ray tube must be placed under high voltage (from 30 to about 150 kV) and strong currents (up to 1 amperes).

High-voltage elements, if not properly insulated from their environment, can discharge current locally in a phenomenon called "arcing." Lightning is the most obvious type of natural arcing where current from clouds at high voltage jumps through the insulating atmosphere to the earth. X-ray tubes at high voltage arc on the interior glass in an effect called "crazing" because the conductive tungsten or molybdenum migrates from the anode to the inner surface of the glass bulb and forms a conductive deposit layer. Anodes and cathodes, the elements of the system placed at the greatest energetic strain, can also arc as any high-voltage power supply for all of the reasons well known to those skilled in the art, including, for example, when partial electrical insulation weakens over time. As a consequence, CT scanners may arc at least three known locations: the x-ray tube, the anode high-voltage tank, and the cathode high-voltage tank.

Some CT scanners place the anode and cathode at opposite polarities to protect the rest of the system. For example, polarities might be set at +70 kV and −70 kV to create a voltage variation in the lamp of 140 kV. Other scanners ground the anode or the cathode and increase the voltage of the opposite element to ±140 kV. When an arc is created, the sudden, rapid discharge releases powerful energy to a different portion of the system, and as an immediate result, secondary effects are created in the system. Once an arc discharges locally, power is transferred rapidly from one of the energized component to its grounded casing or grounded shield with an associated drop in voltage for a short period of time. As the energy propagates in the structure, a series of rapid reflections are created afterward.

As electrons move and the voltage drops quickly to near zero, this variation disturbs the magnetic field located around the structure, which in turn creates a secondary current, and so forth. These secondary effects, or "ripple" effects, are known to lead to the creation of secondary arcs at different locations from the primary arc, which make detection of the location of the arc very difficult to diagnose using conventional methods.

Known technologies used to diagnose the origin of arcs include the use of sound detectors within the proximity of the x-ray tube, the anode high-voltage tank, and the cathode high-voltage tank. Since electrical discharges propagate faster than the speed of sound in air, a sonic shockwave may be created upon discharge. If the arc occurs in a solid, liquid, or semisolid, such as between layers of an insulated cable, low-frequency noise can be heard. Because CT scanners are very noisy and noise detection is often very difficult between closely positioned elements, conventional methods are unreliable to measure the primary arc and diagnose secondary arcs occurring as a result of the primary arc.

CT scanners also are equipped with their own arc detection modules. These modules cannot distinguish where arcs occur and how to differentiate between primary spit events and secondary spit events, which are defined to include but are not limited to induced arcs created as a result of the primary arc within the system.

To perform adequate maintenance on a CT scanner, the defective element must be known. What is needed is a system and apparatus to measure arcs either on the x-ray tube, the anode, or the cathode with a high degree of precision, to diagnose faults, and to predict failure of the main high-voltage components of the CT scanner.

SUMMARY

The present disclosure relates to an impedance-based arc detector for CT scanners and a method of use and diagnosis therewith, and more specifically, to a two- or three-way conductive probe detector system and associated signal processing unit to distinguish the location of arc faults on a CT scanner either at the high-voltage cable of an x-ray tube, an anode connected to the x-ray tube, a cathode also connected to the x-ray tube, a high-voltage well, or a power distribution unit of the tube.

BRIEF DESCRIPTION OF THE DRAWINGS

Certain embodiments are shown in the drawings. However, it is understood that the present disclosure is not limited to the arrangements and instrumentality shown in the attached drawings, wherein.

DETAILED DESCRIPTION

The present invention is not limited to the particular details of the device depicted, and other modifications and applications may be contemplated. Further changes may be made in the device described herein without departing from the true spirit of the scope of the disclosure. It is intended, therefore, that the subject matter of the above depictions should be interpreted as illustrative, not in a limiting sense.

Current and tension fluctuations, such as those resulting from a sudden discharge, create strong variations in the overall electrical and induced magnetic fields and their properties on a high-voltage systems. Bodies, such as electrical cables, oppose changes in current as embodied in the Maxwell equations through a property called "electrical impedance," or more simply, "impedance." Discharges occurring in Direct Current (DC) systems or a transitory Alternate Current (AC) often take the form of a ripple or a resonance from a baseline value. If a first component in a system discharges, an AC current can be created within a secondary conductor if it is coiled around a first conductor placed in proximity with the discharging component. If the conductor is coiled in one direction, the resonance is polarized in one direction; if the conductor is coiled in the opposite direction, the resonance is polarized in the opposite direction.

As the first conductor's voltage changes, a magnetic field is created, which acts in turn upon the second conductor to force a current analogous with a voltage change. As a result, induced transfer of AC current from the primary conductor to the secondary conductor can be measured along with a phase shift and/or a time shift if the conductors are orthogonal. The AC current ripple or resonance also propagates along the primary and secondary conductors at known speeds.

The shockwave of arc-induced current, also known in high-voltage systems as a "primary spit event," also propagates within a system and can reflect or bounce back along the conductor several times as the event migrates back and forth from assembly to assembly, possibly causing these assemblies to discharge or arc in what are called "secondary spit events," which result in subsequent phased AC pulses. Secondary spit events can also be caused by increased voltage at points as the resonance migrates to the different assemblies in the system.

Figure 1:
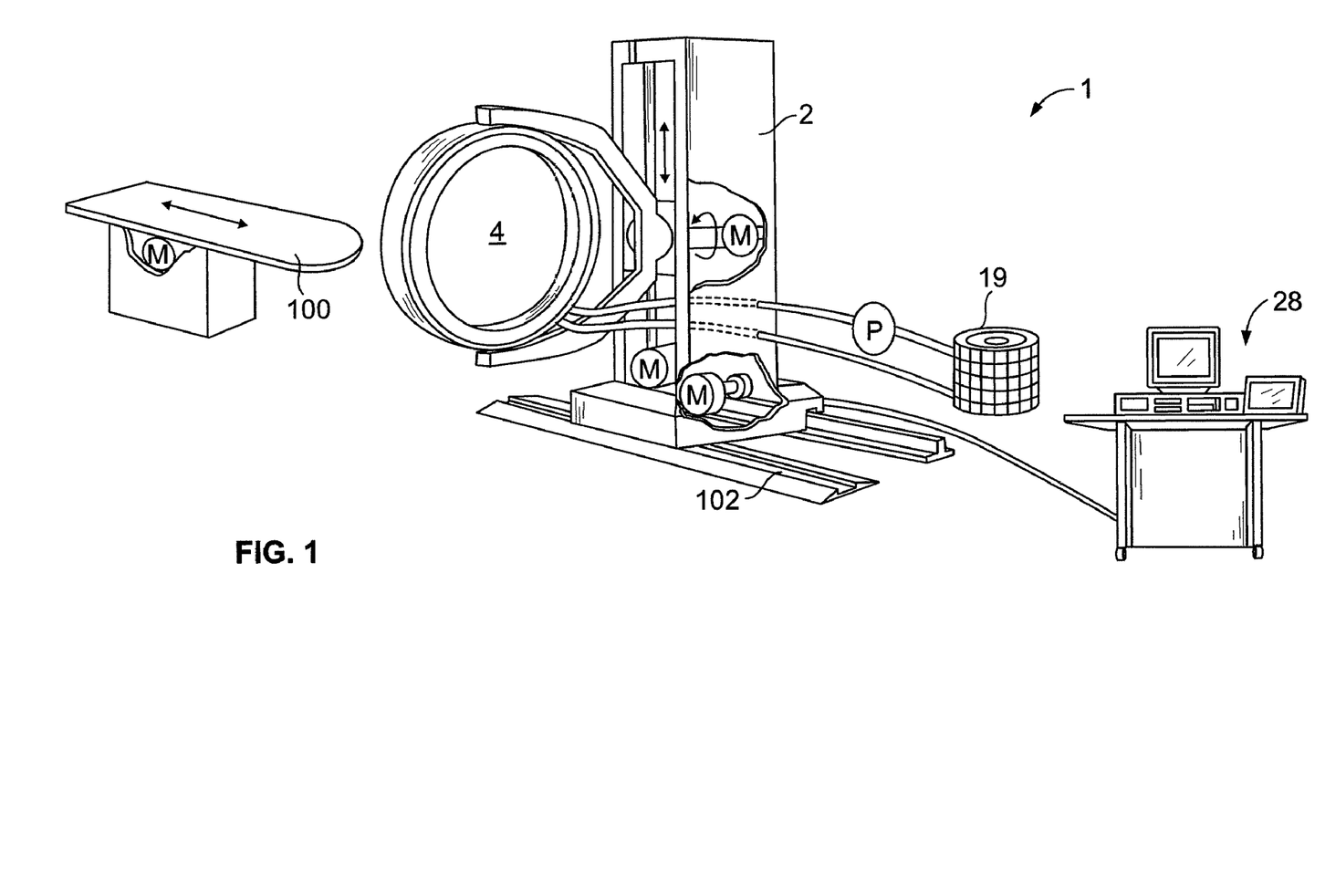
FIG. 1 is a perspective view of the different components of a CT scanner according to an embodiment of the present disclosure.
Figure 2:
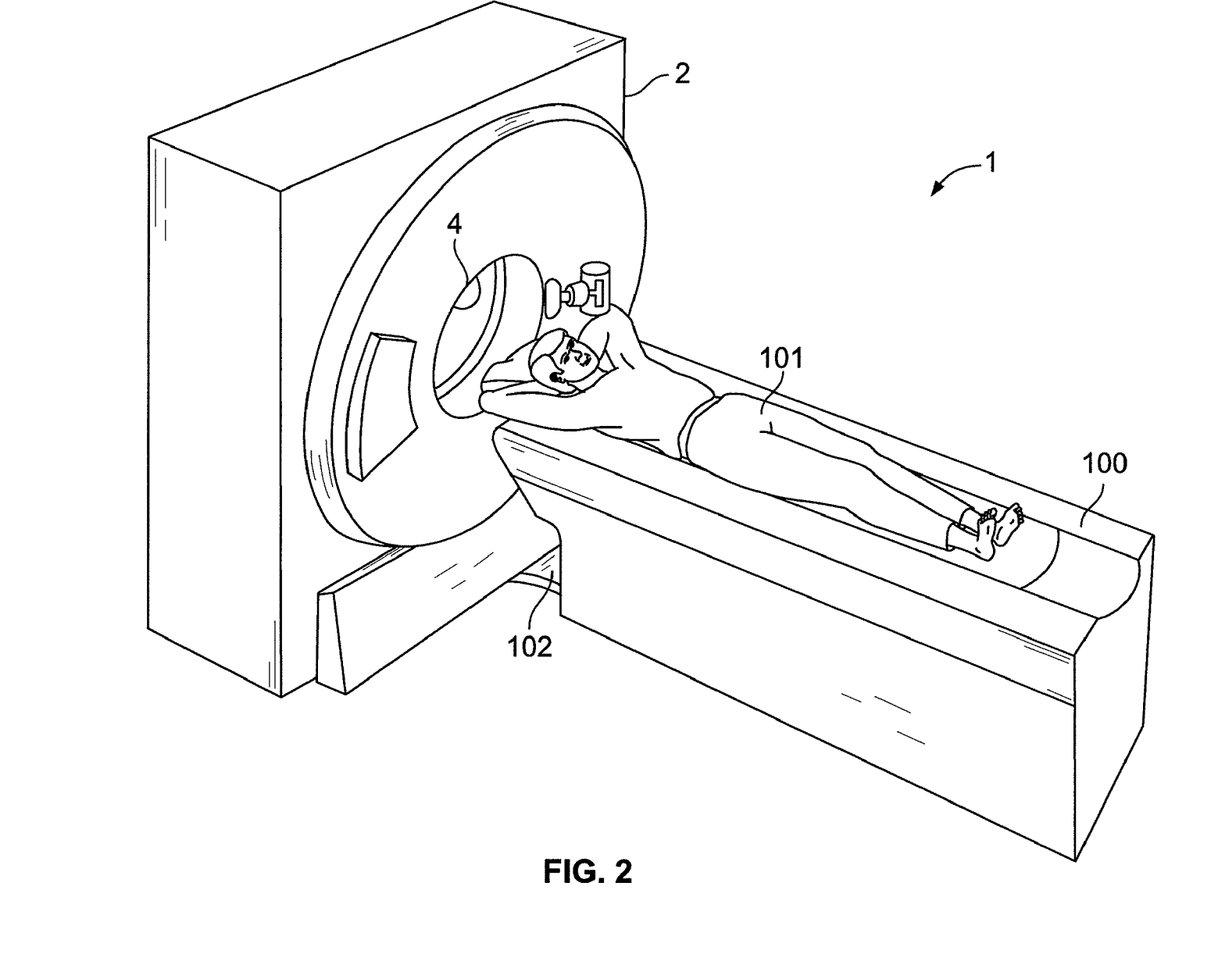
FIG. 2 is a perspective view of a conventional, single-block CT scanner according to another embodiment of the present disclosure.

The x-ray generator of a CT scanning system is located inside a rotating gantry (i.e., a large, circular device with center opening 4 as shown in FIGS. 1 and 2. An x-ray generator rotates around an imaging bore during data acquisition. FIG. 1 shows how a table 100 can be made to move in the direction illustrated by the arrow using a motor M. The patient 101 as illustrated in FIG. 2 is then either slid through the center opening 4 or the entire CT scanner is made to move along rails 102 until the gantry passes over the patient, immersing him or her in a flow of x-ray waves.

In FIG. 1, motors M can be used to translate the CT scanner 2 up or down, front and back, and a cooling system 19 can be used along with a pumped fluid to cool off the gantry. Finally, an arc detection module (ADM) 28 can be used and is shown with a keyboard, a computer display, and cables connected to the CT scanner. FIG. 2 shows a compact CT scanner 2 where the gantry is fixed and the patient 101 is slid into the device on rails 102. While two different types of CT scanning systems 2 are shown, what is contemplated is the use of the described invention in conjunction with any known CT imaging technology and/or device.

Figure 3:
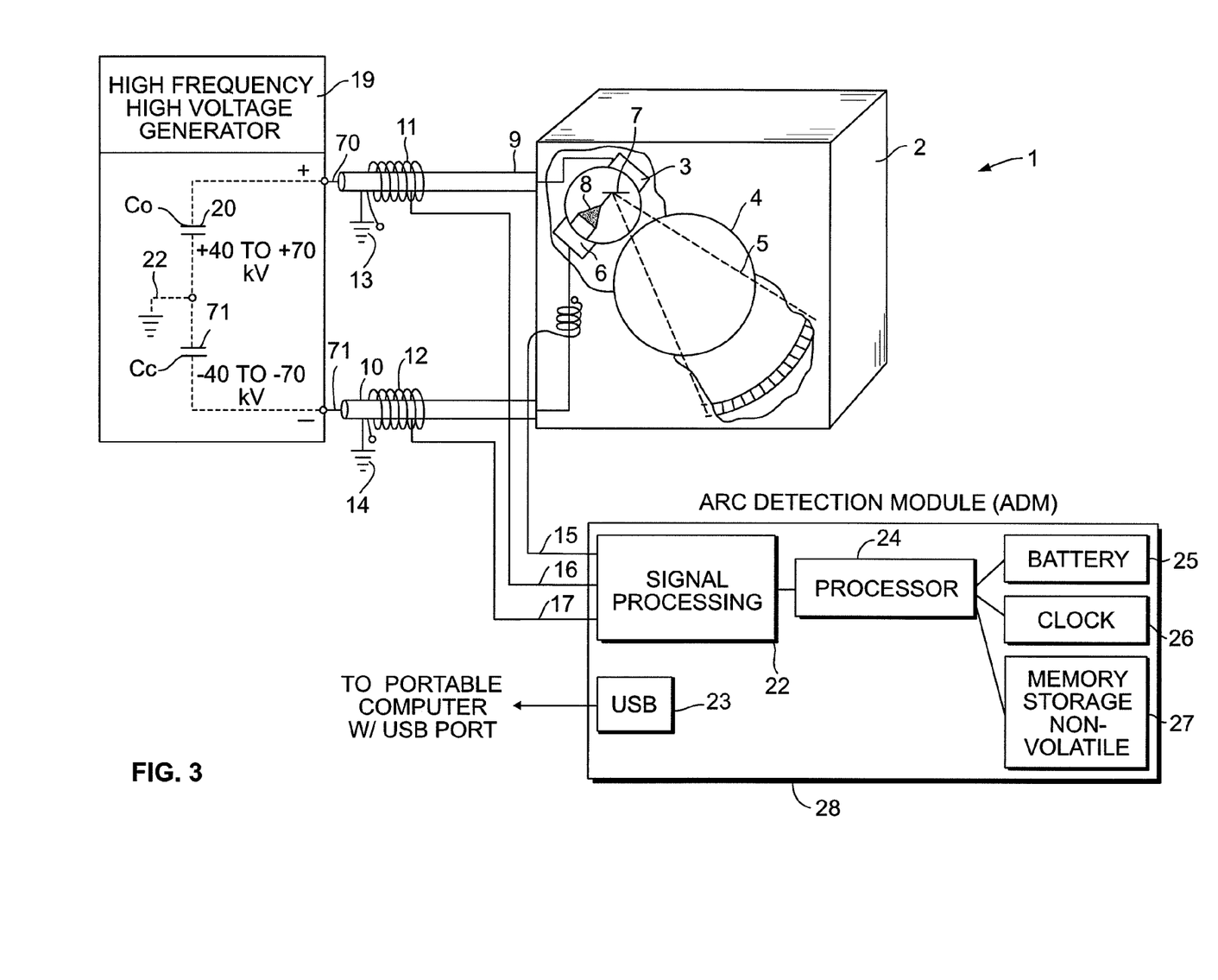
FIG. 3 is a functional diagram of the impedance-based arc detector for CT scanners according to an embodiment of the present disclosure.

FIG. 3 shows a functional diagram of the impedance-based arc detector 1 for CT scanners 2 according to an embodiment of the present disclosure. A CT scanner 2 is generally shown as a large device with a center opening 4 where patients are inserted using beds placed on horizontal rollers as shown in FIGS. 1 and 2. An x-ray tube 3 having a cathode 6 and an anode 7 allows electrons 8 to flow from the cathode 6 to the anode 7, and as a result, generate perpendicular x-rays 5 that pass through the center opening 4, irradiating the subject patient (not shown).

Figure 5:
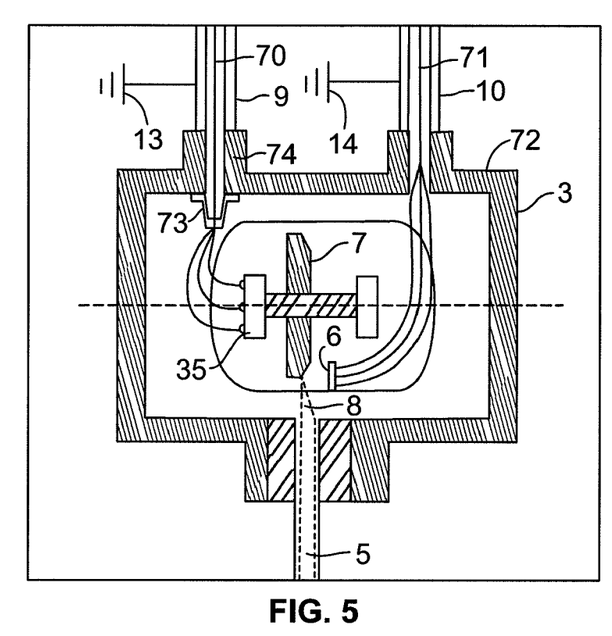
FIG. 5 is a close-up view of an x-ray tube according to an embodiment of the present disclosure.

FIG. 5 shows a close-up view of a sample x-ray tube 3 where electrical conductors 70, 71, such as a first conductor 71 and a second conductor 70, are protected and insulated in grounded insulations 9, 10. A ground is shown in FIG. 5 as elements 13, 14. The x-ray tube is protected by a casing 72 and the high-voltage conductors 70, 71 may be connected via a high-voltage well 73 at a connector 74. In the x-ray tube 3 shown in FIG. 5, only the anode side includes a well 73. What is contemplated is the use of high voltage at either of the anode and cathode 6, 7, or a greater potential at only the anode and cathode (as shown).

Returning to FIG. 3, in one embodiment, the cathode 6 is connected via a first conductor 71 to a negative voltage source 21 ranging from −40 kV to −70 kV. The anode 7 is also connected via a second conductor 70 to a positive voltage source 20 ranging from +40 kV to +70 kV. As a result of a positively and negatively charged anode 7 and cathode 6, the voltage difference on the x-ray tube 3 is a total of 80 kV to 140 kV. While a positively and negatively charged high-voltage generator 19 is shown, the use of any voltage variation that results in a voltage differential at the x-ray is contemplated.

In FIG. 3, the first and second conductors 70, 71 are insulated 9, 10. The x-ray tube 3 housing is also grounded (not shown): The impedance-based arc detector 1 includes three sensors 15, 16, and 17, each connected to a signal processing unit 22 located within the ADM 28. In one contemplated embodiment, the sensor 17 connecting the first conductor 71 is wrapped around 12 the insulation 10, the sensor 16 is wrapped around 11 the insulation 9, and the sensor 15 is wrapped around the insulation (not shown) of the tube 3 conductor. While a configuration where the sensors 15, 16, 17 are coiled around the different insulations 9, 10 is shown, for example, to enhance the impedance of the conductor, the use of any configuration that allows for the measure of fluctuations in current within the sensors 15, 16, 17 resulting from the arc discharge is contemplated.

Figure 6:
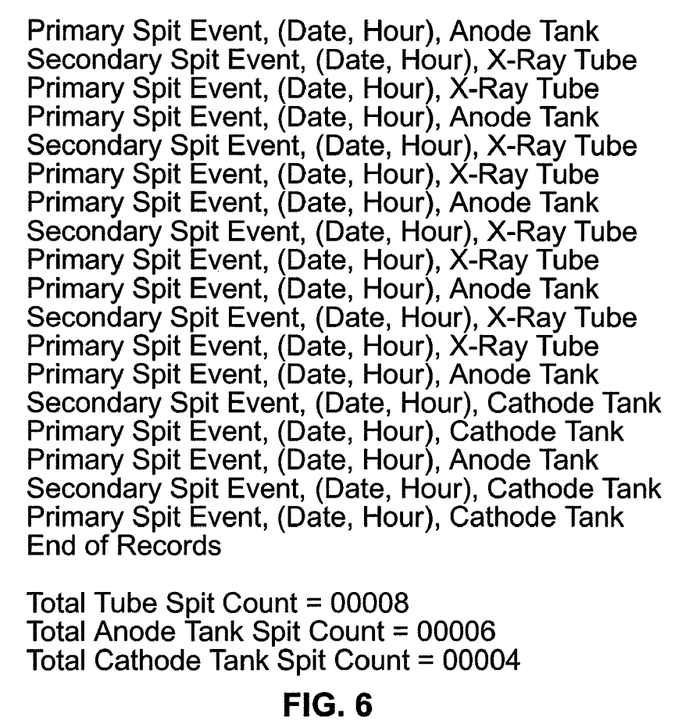
FIG. 6 is a sample printout of the CT scanner system arc/spit report generated during a one-minute test of a CT scanner.

The ADM 28 can also include a processor 24, a battery 25, a clock 26, and a nonvolatile memory storage unit 27. The module 28 can also include a communication port, such as a USB port 23, to connect the ADM 28 to a laptop (not shown) or any other external data processing unit capable of interface with a user. FIG. 6 shows a sample printout of the CT scanner system arc/spit report generated during a one-minute test of a CT scanner. On this printout, the ADM 28 and post-processing unit can prepare a report where proprietary information is given along with a timestamp of the different primary arc/spit and secondary arc/spit events measured along with a calculation of total arc/spit for the tube, the anode high-voltage tank, and the cathode high-voltage tank.

Figure 7:
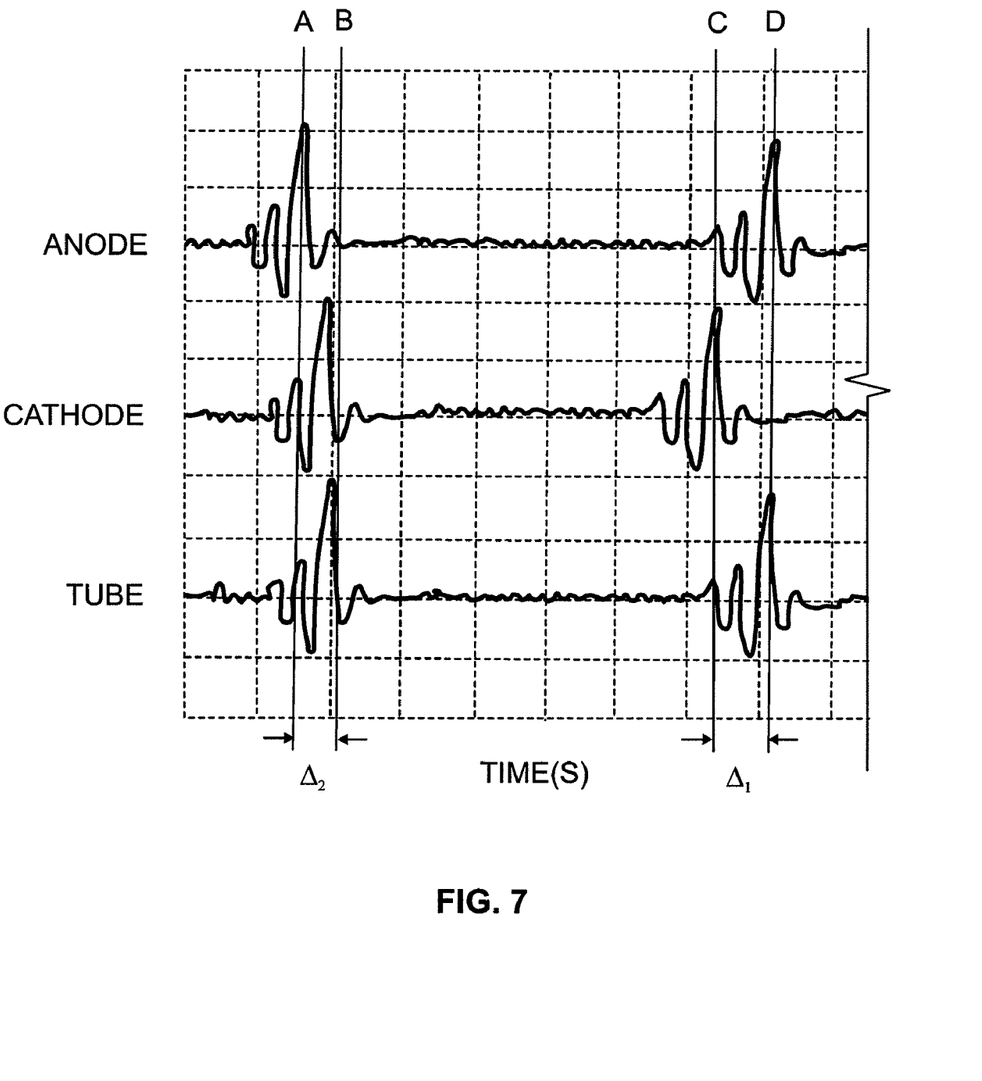
FIG. 7 is a sample current impedance-induced pulse-variation measurement as perceived by the sensors showing a time shift between the measure at the different probes as the result of a first arc and a second arc according to an embodiment of the present disclosure.

FIG. 7 shows a sample printout or a display image of the impedance current measured within the three conductors 15, 16, 17 connected to the x-ray tube 3, the anode 7, and the cathode 6, respectively. An arc or a primary spit event is read in this figure at time A at the anode 7. In a small off-set $\Delta_2$, an induced pulse is measured on both of the other conductors a small fraction of time later. In one embodiment, what the curves show is a time lag between the curves of a approximately 100 nanoseconds. In this case, the primary spit event is on the anode 7, and the secondary spit events are on the x-ray tube 3 and the cathode 6. On the right side of FIG. 7, a second primary spit event is recorded on the cathode 6 off-set temporarily by $\Delta_1$. This time, the resonance occurs at the x-ray tube 3 and the anode 6. The primary spit event is recorded by the processor 24 at the cathode 6, and the secondary spit events are recorded on the tube 3 and the anode 3. While a configuration where the two secondary spits are recorded, it has been observed that secondary spit events do not happen constantly or at a single secondary location. What is contemplated is the measure of any primary spit event or secondary spit event, calculated as shown in FIG. 6, where secondary spits are discarded to ultimately determine the total number of primary spit events at each of the locations under analysis.

Figure 8:
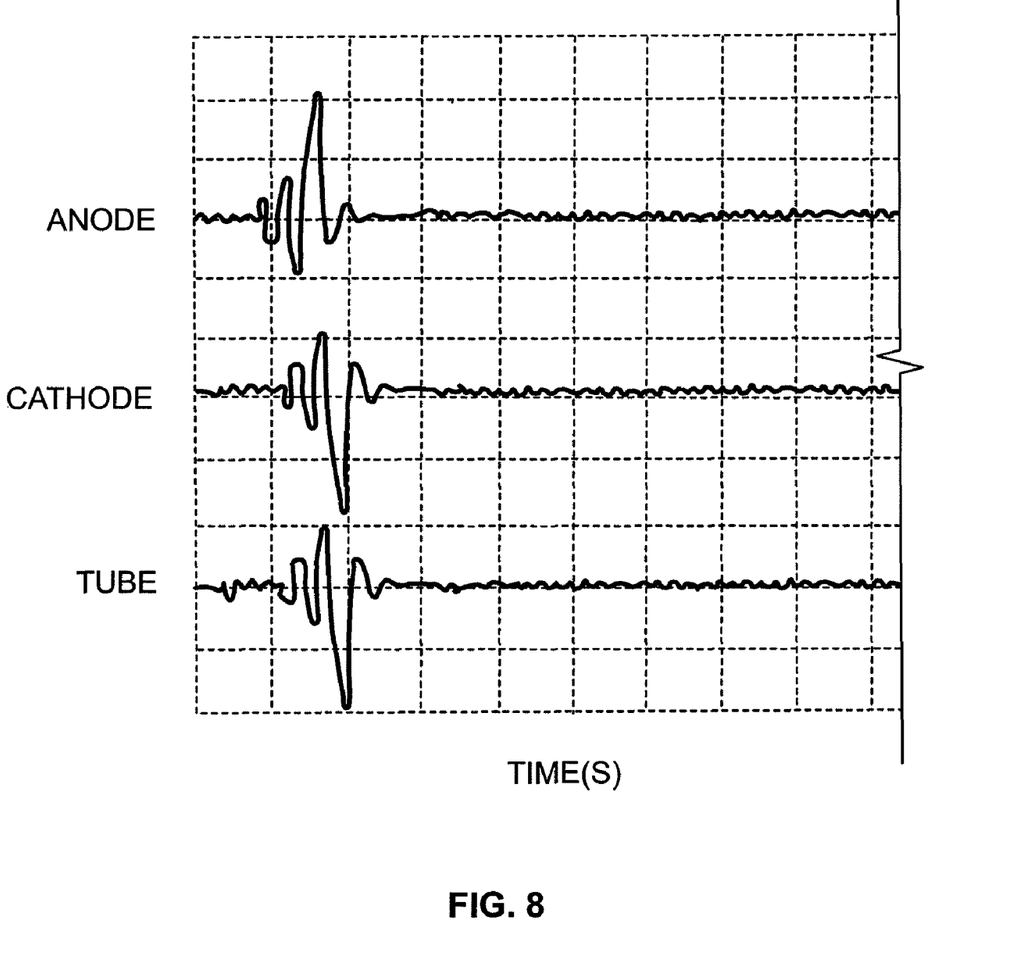
FIG. 8 is a sample current impedance-induced pulse-variation measurement as perceived by the sensors showing a phase shift between the measure at the different probes as the result of a first arc and a second arc according to another embodiment.

FIG. 8 illustrates a situation where instead of the secondary spits measured at an off-set time variation or a time lag from the primary spit, a out of phase induced current is measured. The anode 7 arcs and both the cathode 6 and x-ray tube 3 are out of phase (i.e., the maximum positive current variation at the anode 7 induces the minimum current variation at the cathode 6 and the x-ray tube 3. Induced currents are a byproduct of a distance from a source of arcs, the orthogonal or parallel orientation of the sensor conductor when compared to the source of the arching source, the thickness of insulation between the arcing source and the coiled sensor, the conductivity of the coiled sensor, and many other parameters generally known in the art of measuring inductive currents from primary conductors. One of ordinary skill in the art will recognize that while FIGS. 7 and 8 describe several possible induced measures, actual measures may be a combination of different effects to produce an induced current in the sensor that may be partly out of phase, partly off-set temporarily, or partly warped in amplitude.

Figure 4:
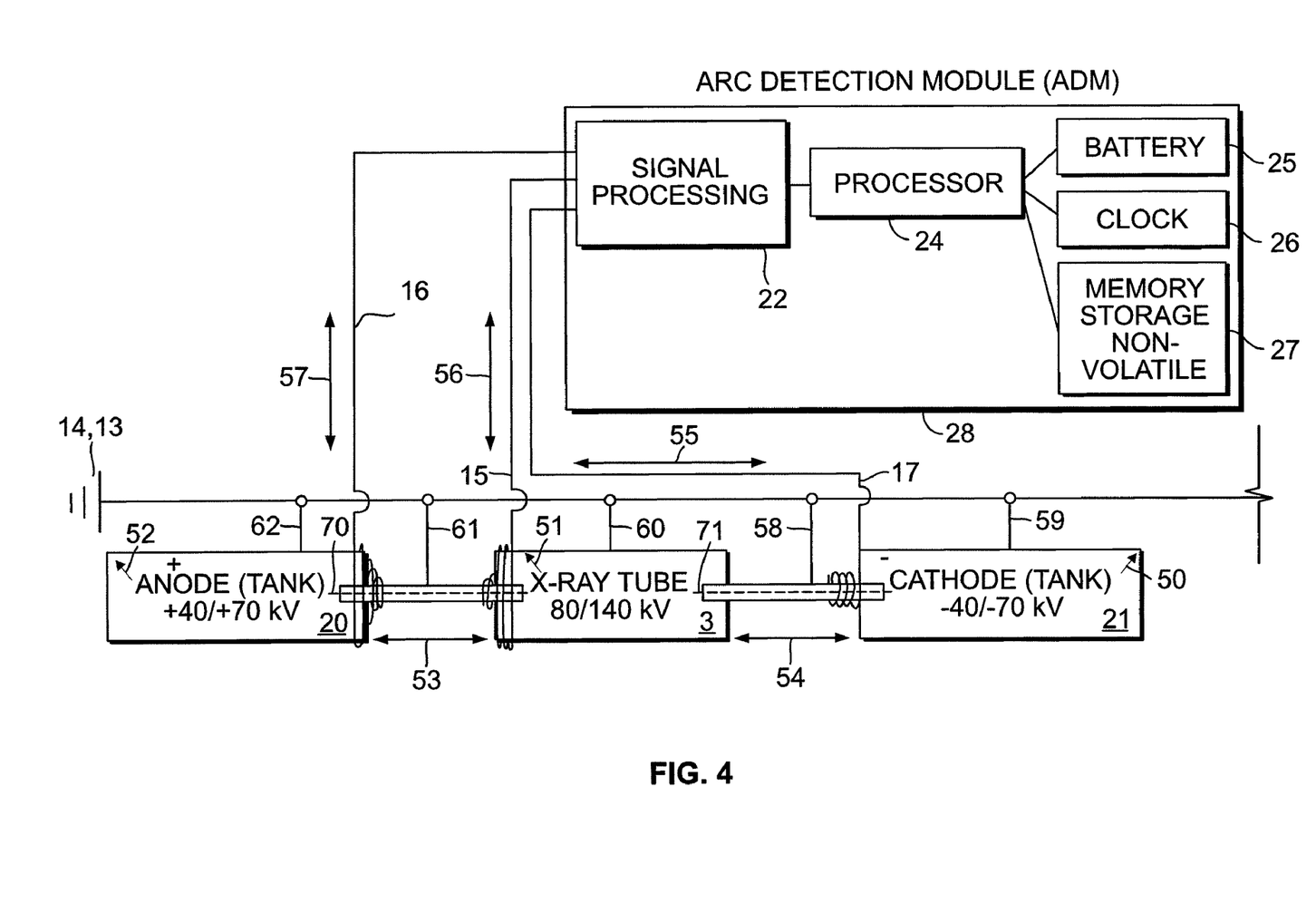
FIG. 4 is a functional diagram of the different arcs and induced currents between the different probes and portions of the system shown in FIG. 3 according to an embodiment of the present disclosure.
Figure 9:
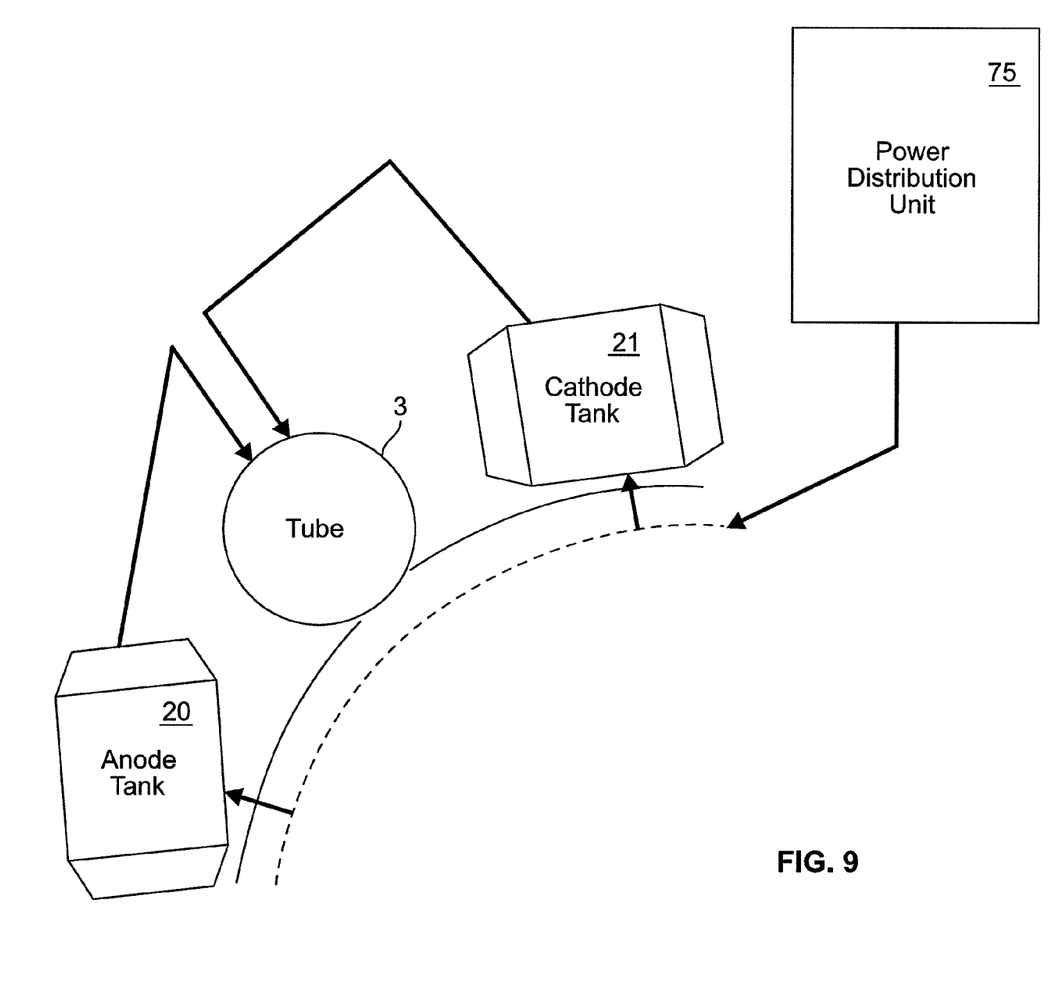
FIG. 9 is an illustration of the different elements on a CT scanner gantry to be tested and diagnosed using the device described in FIG. 3.

FIG. 4 is a functional diagram illustrating the location of the different arcs and induced currents between the different probes and portions of the system shown in FIG. 3 according to an embodiment of the present disclosure. Small arrows 50, 51, 52 represent arcs between the x-ray tube 3, the anode tank 20, the cathode tank 21, and their respective casings or tanks. FIG. 9 illustrates one possible configuration where a power distribution unit 75 is connected to a nonrotating portion of the gantry (shown by dashed lines) where power is transferred to the cathode tank 21 and the anode tank 20 for energizing the x-ray tube 3. The ADM 28, as configured to measure arcs or spit events at the tube 3, the anode 7, the cathode 6, an anode tank 20, or cathode tank 21, can also measure failures indirectly at other parts of the system, such as but not limited to the power distribution unit 75 or the high-voltage well 73 of connectors 74 of the x-ray tube 3.

Returning to FIG. 4, the anode tank 20 is connected to a ground 13, 14 via a conductor 62, much like the cathode tank 21 is also connected to the ground 13, 14 via a conductor 59. Arrows 53 and 54 illustrate how the induced AC current can propagate back and forth between the different elements of the system, possibly causing secondary arcs or spits. Arrows 55, 56, and 57 show how the three sensors 15, 16, 17 of the ADM 28 are also dynamically connected to the different elements of the system as described above and can monitor the different induced currents resulting from primary and secondary discharges.

The impedance-based arc detector 1 for a CT scanner 2 comprises a first conductor, such as sensor 15 coiled around the a high-voltage power cable of the x-ray tube 3, a second conductor, such as sensor 16 coiled around the anode high-voltage power supply tank 20, a third conductor, such as sensor 17 coiled around the cathode high-voltage power supply tank 21, and an ADM 28 electrically connected to the first, second, and third conductors 15, 16, 17 for detecting an impedance-driven current in one of the three conductors or two conductors at three different locations 70 and 71 at a source of a primary arc.

What is contemplated is an impedance-based arc detector 1 for a CT scanner 2 with an arc detection module 28 having a power source 25, such as a battery, a signal processor 22 electrically connected to the power source 25 for energizing said signal processor 22, and at least three electrical conductors 15, 16, 17 as shown in FIG. 3, each electrically connected to the signal processor 22 for reading an impedance-based signal 55, 56, 57 as shown in FIG. 4 within at least one of the electrical conductors. The first conductor 15 is coiled around a high-voltage power cable of an x-ray tube 3 of a CT scanner 2 for reading an induced signal at the high-voltage power cable of the x-ray tube 3, the second conductor 16 is coiled around a high-voltage cable of an anode tank 20 of the x-ray tube 3 for reading an induced signal at the high-voltage power cable of the anode tank 20 or the anode directly 7, and the third conductor 17 is coiled around a high-voltage cable at a cathode tank 21 of the x-ray tube for reading an induced signal at the high-voltage cable at the cathode tank 21 or the cathode directly 6.

The impedance-based signal read by the signal processor 22 is at least one of the induced signals at the high-voltage power cable 56 of the x-ray tube 3, the induced signal at the high-voltage power cable 57 of the anode tank 20, or the induced signal at the high-voltage cable 58 at the cathode tank 21. The ADM 28 in another embodiment comprises a non-volatile memory storage 27, a clock 26, and a battery 25, each functionally connected to the processor 24. The use of non-volatile storage 27, such as a hard drive, allows for the storage of information, data, and software to help the processor 24, in conjunction with the clock 26, to create timed input signals at the signal processing unit 22 to diagnose and manage the different methods described below with greater specificity. A USB port 23 or any other external port can be used on the ADM 28 to export or connect a portable device such as a portable computer or any other device to the ADM 28.

The processor 24 of the ADM 28 processes a time difference $\Delta_1$, $\Delta_2$ between a primary spit event and a secondary spit event as shown in FIG. 7 to determine the origin of an arc when a plurality of arcs are received at the ADM 28 or at an arc detector module 800 as part of the CT scanner 2. In another embodiment, the processor 24 of the ADM 28 processes a change in phase between a first event and a second event to determine the primary spit event as shown in FIG. 8.

In yet another embodiment, the processor 24 of the ADM 28 determines a primary spit event from a change in phase and a time difference between a first event and a second event. In another embodiment, the signal processor 24 measures a plurality of spit events over a fixed period of time, such as, for example one minute, and diagnoses a prevalent source of the arcs based on a frequency of spit events at the prevalent source or the source with the greater number of primary spits events recorded as shown in FIG. 6 where the tube spit count is 8, the anode tank spit count is 6, and the cathode spit count is 4. In the example shown in FIG. 6, the prevalent source would be the x-ray tube 3.

The use of the ADM 28 on a CT scanner 2 allows for the immediate determination of faults or arcs at the anode 7 or anode tank 20, the cathode 6 or cathode tank 21, or the x-ray tube 3. The ADM 28 indirectly also diagnoses other parts of the CT scanner 2 by observing and recording different types of failures that diverge from the arc detection module 800 of the CT scanner. At least three different methods are contemplated. The first method illustrated in FIG. 10 allows for the diagnosis of arcs at the x-ray tube 3, the anode 7 or anode tank 20, and the cathode 6 or the cathode tank 21.

Figure 10:
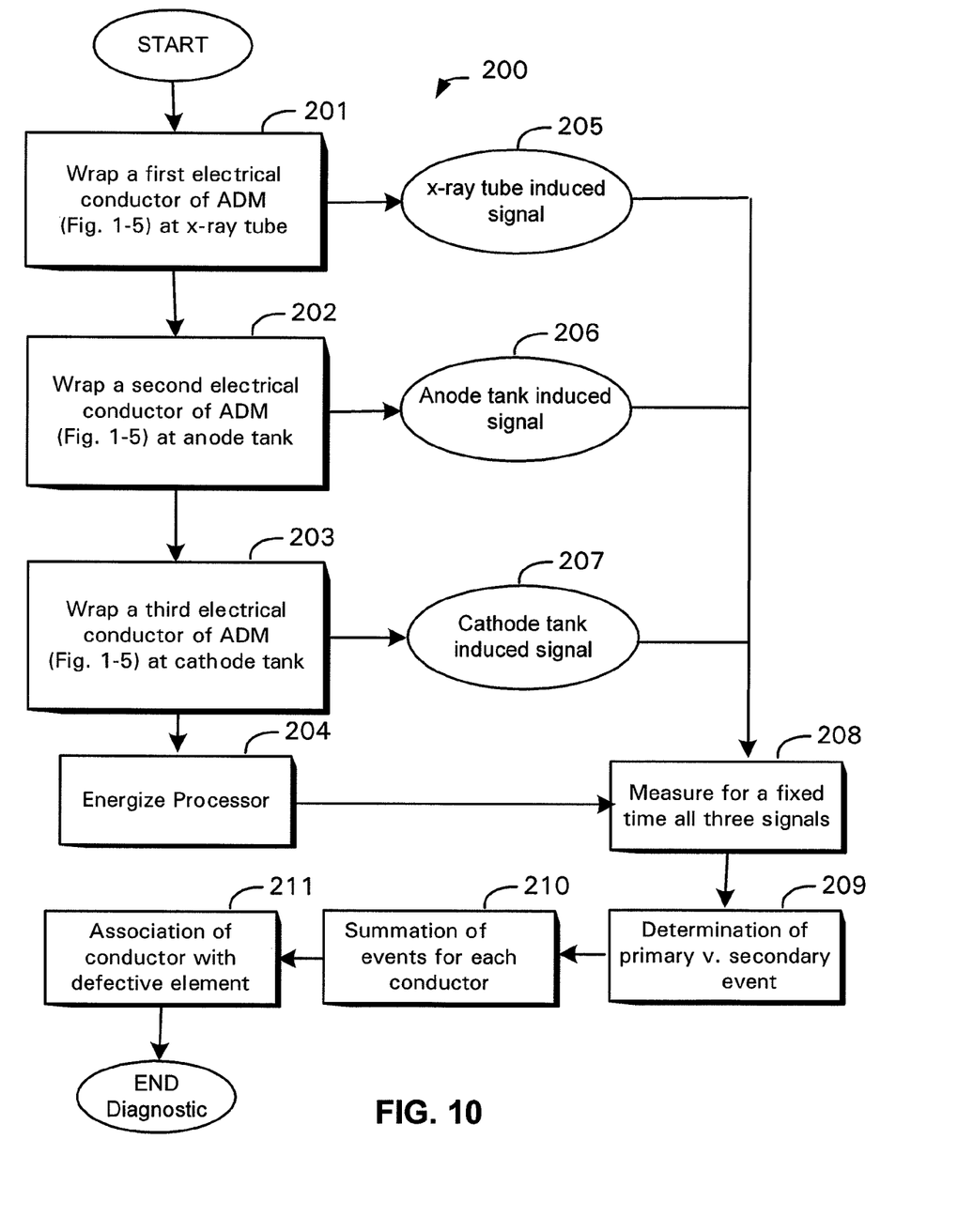
FIG. 10 is a diagram of a method for detecting a defective element in a CT scanner.

A method 200 for detecting a defective element in a CT scanner 2 is described, the method comprising the steps of wrapping 201 a first 15 of at least three electrical conductors 15, 16, 17 of an arc detection module 28 having a power source 25, a signal processor 24 electrically connected to the power source 25 for energizing said signal processor 24, and at least three electrical conductors 15, 16, 17, each electrically connected to the signal processor 24 for reading an impedance-based signal 56 within at least one of the electrical conductors around a high-voltage power cable of an x-ray rotor 3 of a CT scanner 2 for reading an induced signal 205 at the high-voltage power cable of the x-ray tube 3, then wrapping 202 the second 16 of the at least three electrical conductors 15, 16, 17 around a high-voltage cable of an anode tank 20 of the x-ray tube 3 for reading 206 an induced signal at the high-voltage power cable of the anode tank 20, wrapping 203 the third 17 of the at least three electrical conductors 15, 16, 17 around a high-voltage cable at a cathode tank 21 of the x-ray tube 3 for reading an induced signal at the high-voltage cable at the cathode tank 21.

Next, the method includes the steps of energizing 204 the signal processor 24 for measuring 208 over a fixed length of time all of the induced signals (as shown by the arrows) of the at least three electrical conductors 15, 16, 17, and determining 209 if an event is a primary spit event or a secondary spit event by correlating a first induced signal with at least one subsequent induced signal and discarding any subsequent induced signals from a total spit count if a secondary spit event is a resonance of the primary spit event. Finally, the method includes the steps of adding 210 for the fixed length of time all of the primary spit events measured for each of the three electrical conductors 15, 16, 17 to determine the total spit event count for each of the x-ray tube 3, the cathode tank 20, and the anode tank 21, and associating 211 with the x-ray tube 3, the cathode tank 20, and the anode tank 21 having the greatest number of total spit events for the fixed length of time a status of defective element.

Figure 11:
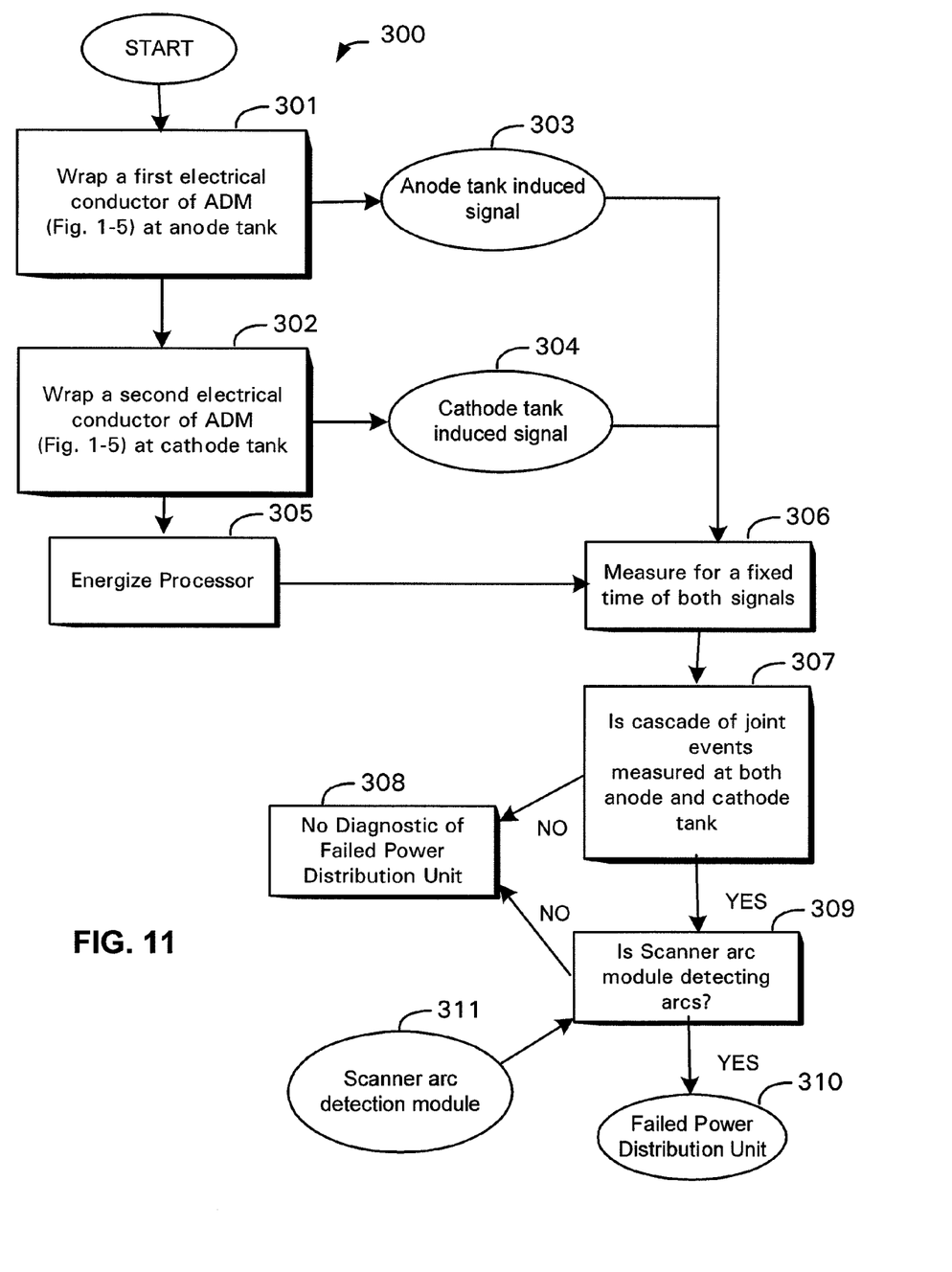
FIG. 11 is a diagram of a method for detecting a failure in a power distribution unit of a CT scanner equipped with a scanner arc detection module.

The second method is illustrated at FIG. 11 and is directed to the diagnosis of failures or arcs produced in the power distribution unit 75. A method 300 for detecting failures in a power distribution unit 75 of a CT scanner 2 equipped with a scanner arc detection module 800 is described, the method having the steps of wrapping 301 a first 16 of at least two electrical conductors 16, 17 of an ADM 28 having a power source 25, a signal processor 24 electrically connected to the power source 25 for energizing said signal processor 24, and at least two electrical conductors 16, 17, each electrically connected to the signal processor 24, for reading an impedance-based signal within at least one of the electrical conductors 16, 17 around a high-voltage cable of an anode tank 20 of the x-ray tube 3 for reading an induced signal at the high-voltage power cable of the anode tank 21.

Next, the method 300 includes the steps of wrapping 302 the second 17 of the at least two electrical conductors 16, 17 around a high-voltage cable at a cathode tank 21 of the x-ray tube for reading an induced signal at the high voltage cable at the cathode tank 21, energizing 305 the signal processor 24 for measuring 306 over a fixed length of time, such as one minute, the induced signals 303, 304 at the at least two electrical conductors 16, 17, wherein a cascade 307 or a plurality of joint spit events are measured at both the first 16 and the second 17 electrical conductors, and a scanner arc detection module 800 of the CT scanner fails to measure any spit 309.

In another embodiment, the AMD 28, like the above-described method, includes at least three electrical conductors 15, 16, 17, each electrically connected to the signal processor 24 for reading an impedance-based signal, and the third electrical conductor 15 is wrapped around a high-voltage power cable of an x-ray rotor 3 of a CT scanner for reading an induced signal at the high-voltage power cable of the x-ray tube 3, and wherein no spit event is measured at the third electrical conductor 15.

Figure 12:
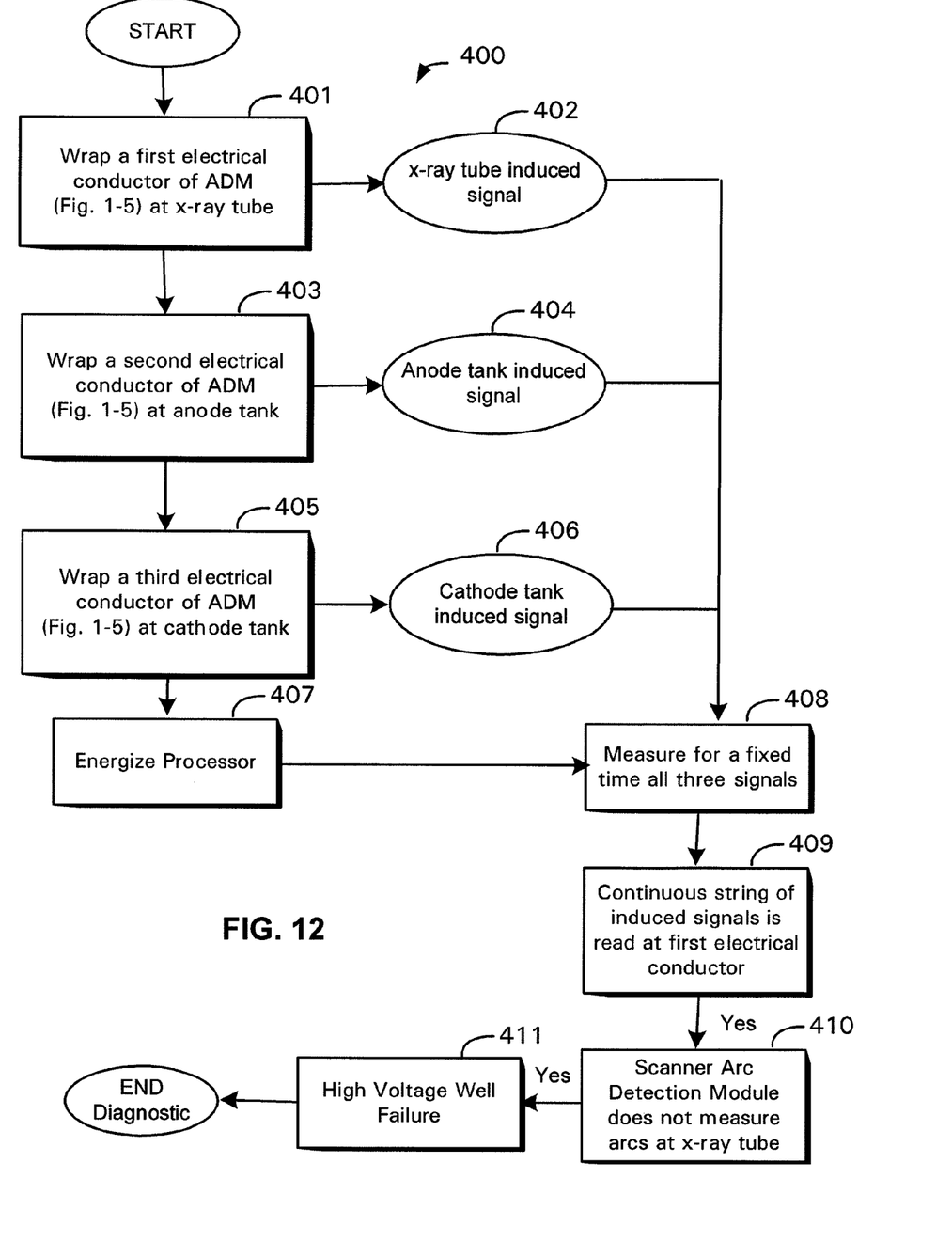
FIG. 12 is a diagram of a method for detecting a failure in a high-voltage well of a CT scanner equipped with a scanner arc detection module.

A third method is illustrated at FIG. 12 and is directed to the diagnosis of failures or arcs produced in the high-voltage well 73 power distribution unit 75. A method 400 of detecting a failure in a high-voltage well of a CT scanner 2 equipped with a scanner arc detection module 800 is described, the method having the steps of wrapping 401 a first 15 of at least three electrical conductors 15, 16, 17 of an ADM 28 having a power source 25, a signal processor 24 electrically connected to the power source 25 for energizing said signal processor 24, and at least three electrical conductors 15, 16, 17, each electrically connected to the signal processor 24 for reading an impedance-based signal 402, 404, 406 within at least one of the electrical conductors around a high-voltage power cable of an x-ray rotor 3 of a CT scanner 2 for reading an induced signal 402 at the high-voltage power cable of the x-ray tube 2, wrapping 403 the second 16 of the at least three electrical conductors 15, 16, 17 around a high-voltage cable of an anode tank 20 of the x-ray tube 3 for reading an induced signal 404 at the high-voltage power cable of the anode tank 3, and wrapping 405 the third 17 of the at least three electrical conductors around a high-voltage cable at a cathode tank 21 of the x-ray tube 3 for reading an induced signal 406 at the high-voltage cable at the cathode tank 21.

Next, the method includes the steps of energizing 407 the signal processor 24 for measuring over a fixed length of time all of the induced signals 402, 404, 406 at the at least three electrical conductors 15, 16, 17, wherein a continuous string 409 of induced signals is read in the first electrical conductor 15 and wherein a scanner arc detection module 800 of the CT scanner 2 fails to measure any spit 410 at the x-ray tube 3.

Persons of ordinary skill in the art appreciate that although the teachings of the disclosure have been illustrated in connection with certain embodiments and methods, there is no intent to limit the invention to such embodiments and methods. On the contrary, the intention of this disclosure is to cover all modifications and embodiments falling fairly within the scope the teachings of the disclosure.

What is claimed is:

1. An impedance-based arc detector for a CT scanner, comprising:
    an arc detection module having a power source, a signal processor electrically connected to the power source for energizing said signal processor, and at least three electrical conductors, each electrically connected to the signal processor for reading an impedance-based signal within at least one of the electrical conductors,
    wherein the first conductor is coiled around a high-voltage power cable of an x-ray tube of a CT scanner for reading an induced signal at the high-voltage power cable of the x-ray tube, the second conductor is coiled around a high-voltage cable of an anode tank of the x-ray tube for reading an induced signal at the high-voltage power cable of the anode tank, and the third conductor is coiled around a high-voltage cable at a cathode tank of the x-ray tube for reading an induced signal at the high voltage cable at the cathode tank,
    wherein a first impedance-based signal read by the signal processor is at least one of the induced signal at the high-voltage power cable of the x-ray tube, the induced signal at the high-voltage power cable of the anode tank, or the induced signal at the high-voltage cable at the cathode tank to read a primary spit event, and a second impedance-based signal is read by the signal processor is at least one of the induced signal at the high-voltage power cable of the x-ray tube, the induced signal at the high-voltage power cable of the anode tank, or the induced signal at the high-voltage cable at the cathode tank to read a secondary spit event.

2. The impedance-based arc detector for a CT scanner of claim 1, wherein the arc detection module further comprises a nonvolatile memory storage, a clock, and a battery, each functionally connected to the processor.

3. The impedance-based detector for a CT scanner of claim 1, wherein the processor of the arc detection module processes a time difference between a primary spit event and a secondary spit event to determine the origin of an arc.

4. The impedance-based detector for a CT scanner of claim 1, wherein the processor of the arc detection module processes a change in phase between a first event and a second event to determine the primary spit event.

5. The impedance-based detector for a CT scanner of claim 1, wherein the processor of the arc detection module determines a primary spit event from a change in phase and a time difference between a first event and a second event.

6. The impedance-based detector for a CT scanner of claim 1, wherein the signal processor measures a plurality of spit events over a fixed period of time and diagnoses a prevalent source of the arcs based on a frequency of spit events at the prevalent source.

7. A method of detecting a defective element in a CT scanner, the method comprising the steps of
    wrapping a first of at least three electrical conductors of an arc detection module having a power source, a signal processor electrically connected to the power source for energizing said signal processor, and at least three electrical conductors each electrically connected to the signal processor for reading an impedance-based signal within at least one of the electrical conductors around a high-voltage power cable of an x-ray tube of a CT scanner for reading an induced signal at the high-voltage power cable of the x-ray tube;
    wrapping the second of the at least three electrical conductors around a high-Voltage cable of an anode tank of the x-ray tube for reading an induced signal at the high-voltage power cable of the anode tank;
    wrapping the third of the at least three electrical conductors around a high-voltage cable at a cathode tank of the x-ray tube for reading an induced signal at the high-voltage cable at the cathode tank;
    energizing the signal processor for measuring over a fixed length of time all of the induced signals at the at least three electrical conductors, wherein for each of the induced signals read by the signal processor, the signal processor determines if an event is a primary spit event or a secondary spit event by correlating a first induced signal with at least one subsequent induced signal and discarding any subsequent induced signals from a total spit count if a secondary spit event is a resonance of the primary spit event;
    adding for the fixed length of time all of the primary spit events measured for each of the three electrical conductors to determine the total spit event count for each of the x-ray tube, the cathode tank, and the anode tank; and
    associating either the x-ray tube, the cathode tank, and the anode tank a status of defective element the element having the greatest number of total spit events for the fixed length of time.

8. The method of claim 7, wherein the resonance is an induced current offset by a time lag.

9. The method of claim 8, wherein the resonance is a out-of-phase induced current.

10. A method for detecting a failure in a power distribution unit of a CT scanner equipped with a scanner arc detection module, the method comprising the steps of:
    wrapping a first of at least two electrical conductors of an arc detection module having a power source, a signal processor electrically connected to the power source for energizing said signal processor, and at least two electrical conductors each electrically connected to the signal processor for reading an impedance-based signal within at least one of the electrical conductors around a high-voltage cable of an anode tank of the x-ray tube for reading an induced signal at the high-voltage power cable of the anode tank;

wrapping the second of the at least two electrical conductors around a high-voltage cable at a cathode tank of the x-ray tube for reading an induced signal at the high-voltage cable at the cathode tank;

energizing the signal processor for measuring over a fixed length of time all of the induced signals at the at least two electrical conductors, wherein a cascade of joint spit events are measured at both the first and the second electrical conductors, and wherein the scanner arc detection module of the CT scanner fails to measure any spit.

11. The method of claim 10, wherein the arc detection module includes at least three electrical conductors, each electrically connected to the signal processor for reading an impedance-based signal, and the third electrical conductor is wrapped around a high voltage power cable of an x-ray tube of a CT scanner for reading an induced signal at the high-voltage power cable of the x-ray tube, and wherein no spit event is measured at the third electrical conductor.

12. A method of detecting a failure in a high-voltage well of a CT scanner equipped with a scanner arc detection module, the method comprising the steps of:

wrapping a first of at least three electrical conductors of an arc detection module having a power source, a signal processor electrically connected to the power source for energizing said signal processor, and at least three electrical conductors, each electrically connected to the signal processor for reading an impedance-based signal within at least one of the electrical conductors around a high-voltage power cable of an x-ray tube of a CT scanner for reading an induced signal at the high-voltage power cable of the x-ray tube;

wrapping the second of the at least three electrical conductors around a high-voltage cable of an anode tank of the x-ray tube for reading an induced signal at the high-voltage power cable of the anode tank;

wrapping the third of the at least three electrical conductors around a high-voltage cable at a cathode tank of the x-ray tube for reading an induced signal at the high-voltage cable at the cathode tank;

energizing the signal processor for measuring over a fixed length of time all of the induced signals at the at least three electrical conductors, wherein a continuous string of induced signals is read in the first electrical conductor and wherein a scanner arc detection module of the CT scanner fails to measure any spit at the x-ray tube.

* * * * *